(12) United States Patent
Jacobs et al.

(10) Patent No.: US 7,077,154 B2
(45) Date of Patent: Jul. 18, 2006

(54) APPARATUS FOR CONTROLLING THE PRESSURE OF GAS BY BUBBLING THROUGH A LIQUID, SUCH AS BUBBLE CPAP

(76) Inventors: Harris C. Jacobs, 14 Tanglewood La., Woodbridge, CT (US) 06525; Louis S. DeMichiel, 80 Rosedale Ter., Stratford, CT (US) 06614

( * ) Notice: Subject to any disclaimer, the term of this patent is extended or adjusted under 35 U.S.C. 154(b) by 45 days.

(21) Appl. No.: 10/913,665

(22) Filed: Aug. 6, 2004

(65) Prior Publication Data

US 2005/0072470 A1 Apr. 7, 2005

Related U.S. Application Data

(60) Provisional application No. 60/507,715, filed on Oct. 1, 2003, provisional application No. 60/576,674, filed on Jun. 3, 2004.

(51) Int. Cl.
*A62B 9/02* (2006.01)
(52) U.S. Cl. .............................. 137/251.1; 128/201.23; 128/204.18; 128/205.24
(58) Field of Classification Search ............. 137/251.1; 128/204.18, 201.23, 204.29, 205.24, 207.18
See application file for complete search history.

(56) References Cited

U.S. PATENT DOCUMENTS

| | | | | |
|---|---|---|---|---|
| 1,304,327 A | | 5/1919 | Klay | |
| 2,088,720 A | * | 8/1937 | Poliniak | 128/200.13 |
| 2,328,995 A | | 9/1943 | Olds | |
| 2,375,711 A | | 5/1945 | Vondrak | |
| 3,827,433 A | * | 8/1974 | Shannon | 128/201.23 |
| 3,949,749 A | * | 4/1976 | Stewart | 128/204.24 |
| 4,080,989 A | | 3/1978 | Chapelsky et al. | |
| 4,459,983 A | | 7/1984 | Beyreuther et al. | |
| 5,255,675 A | | 10/1993 | Kolobow | |
| 6,041,777 A | * | 3/2000 | Faithfull et al. | 128/204.18 |
| 6,520,021 B1 | | 2/2003 | Wixey et al. | |

* cited by examiner

*Primary Examiner*—John Rivell

(57) ABSTRACT

Apparatus for effecting bubble CPAP. The apparatus includes a hollow vessel holding a liquid, a cap, and a positionable tube assembly. The positionable tube assembly comprises a guide tube and a positionable tube. The positionable tube is arranged to have a gas introduced through it and is located within the guide tube. The positionable tube is arranged to be slid to various discrete longitudinal positions with respect to the guide tube and to be held in any one of those discrete positions against accidental displacement so that the lower free end of the positionable tube is held at a desired position below the surface of the liquid.

14 Claims, 4 Drawing Sheets

APPARATUS FOR CONTROLLING THE PRESSURE OF GAS BY BUBBLING THROUGH A LIQUID, SUCH AS BUBBLE CPAP

CROSS-REFERENCE TO RELATED APPLICATIONS

This application claims priority from our provisional U.S. Patent Application No. 60/507,715, filed on Oct. 1, 2003, and provisional U.S. Patent Application No. 60/576,674, filed on Jun. 3, 2004.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

SPECIFICATION

BACKGROUND OF THE INVENTION

1. Field of Invention

This invention relates generally to apparatus for controlling pressure of a gas in a system that depends on the pressure being produced by bubbling the gas through a liquid, and more particularly to apparatus for effecting bubble continuous positive airway pressure (CPAP).

2. Description of Related Art

Nasal Continuous Positive Airway Pressure (NCPAP) is a well-known technique for providing respiratory support to newborn term and preterm infants with respiratory distress requiring support less aggressive than intubation and mechanical ventilation. The basic mechanism consists of attaching standard infant ventilator tubing to the head of the infant. A pair of nasal prongs, which fit in the infant's nostrils or a face mask which fits over the infant's nose and mouth, are provided between the inflow and outflow limbs of a ventilator tubing. Air flows through the tubing at increased pressure relative to atmospheric pressure by including a partial obstruction at the end of the tubing, beyond the nasal prongs/face mask. The air flowing out of the prongs/face mask is forced into the infant's nasal passages and hence his/her lungs. The amount of respiratory support is a function of the pressure in the ventilator tubing (measured in centimeters of water). It is not described by the amount of flow through the prongs/face mask or by the amount of pressure applied to the lungs, neither of which is known.

There are two typical means of controlling the pressure in the NCPAP tubing. One method is to use a mechanical ventilator which is not set to cycle. Rather it is set to provide continuous pressure. Use of a mechanical ventilator is quite reliable, but increases wear and tear on the ventilator. A dial on the face of the ventilator is adjusted to the desired pressure which is read on a manometer and/or a digital readout.

The second method is called "bubble CPAP" and one typical conventional prior art set-up for effecting it is shown in FIG. 1. Thus, as can be seen in that figure, a supply of oxygen from a wall outlet (not shown) is provided through a section suitable conventional tubing 12 to one input of a mixing chamber 14. A supply of air from another wall outlet (not shown) is provided through another section of suitable conventional tubing 16 to another input of the mixing chamber 14. The oxygen and air are mixed within the chamber 14 and flow out of the chamber into a conventional humidifier 18, where the gas mixture is humidified to the desired humidity. The upstream end of one section or limb 20A of a conventional ventilator tube 20 is connected to the outlet of the humidifier 18. The opposite end of that ventilator tube section is connected to the upstream end of either a pair of conventional nasal prongs 22 or to the upstream end of a conventional face mask 24 (depending on which device is to be used to effect the delivery of the air into the nasal passages of the infant). The downstream end of the pair of prongs 22 or face mask 24 is connected to the upstream end of another section or limb 20B of the ventilator tube 20. The downstream free end 20C of the ventilator tube section 20 is submersed in a liquid 26, e.g., 1.25 ml glacial acetic acid added to 500 ml water (0.25% acetic acid), in a bottle 28 or other hollow vessel. Accordingly, the humidified air flows from the humidifier through the ventilator tube section 20A to either the nasal prongs or face mask (as the case may be) and from there into the lungs of the infant. Uninhaled air flows past the nasal prongs or face mask into the downstream ventilator tube section 20B and out its open end 20C, where the exiting gas forms bubbles 30 which rise to the surface of the liquid 26 and dissipate to the ambient atmosphere.

The depth at which the downstream end 20C of the ventilator tube section 20 is located below the surface of the liquid 26 in the bottle determines the pressure in the ventilator tube 20 at the nasal prongs or face mark (i.e., the amount of respiratory support provided to the infant). This pressure is typically measured by means of a tape strip 32 secured to the bottle. In particular, the tape strip has a scale in the form centimeter markings 34 and associated numeric indicia printed thereon so that the position of the downstream free end 20C can be read off of the scale.

The pressure range in the ventilator tubing 20 is typically varied from 4 to 8 centimeters of water, in 1 centimeter increments, by adjusting the height at which the free end 20C of the ventilator tube 20 is located below the surface of the liquid 26. Once the desired distance below the surface of the liquid has been established the tube section 20B is secured in place by some auxiliary means, e.g., wedged with a syringe (not shown) or some other means to hold its free end 20C at the desired depth in the liquid. A pressure manometer 36 may be used along with or in place of the tape strip to determine the pressure in the ventilator tubing.

As will be appreciated by those skilled in the art, while it is possible using a conventional bubble CPAP set-up like that shown in FIG. 1 to place an infant on 5 centimeters of CPAP or 6 centimeters of CPAP, intermediate and finer adjustments, e.g., 5.5 centimeters of CPAP, are not practical. Thus, while the system is an analog one, changes are typically made in whole centimeter increments. Moreover, the use of bubble CPAP requires more diligence for reliability. Specifically, no reliable method for insuring the depth of insertion of the ventilator tube in the liquid is available. Hence the tube may slip in or out inadvertently which changes the pressure in the ventilator tubing to the infant.

Accordingly a need exists for a bubble CPAP system which overcomes the disadvantages of the prior art.

BRIEF SUMMARY OF THE INVENTION

Apparatus for controlling pressure of a gas in a system that depends on the pressure being produced by bubbling the gas through a liquid. The apparatus comprises a hollow vessel, a cap, and a positionable tube. The hollow vessel is arranged to have a predetermined amount of the liquid in it, whereupon the surface of the liquid is at a predetermined height in the vessel. The cap is located above the surface of the liquid and includes an opening through which the positionable tube extends. The positionable tube also includes a proximal portion arranged to be coupled to a source of the gas, whereupon the gas may flow into and through the positionable tube. The positionable tube includes a distal portion which is generally linear and terminates at an outlet port through which the gas may exit to bubble up through the liquid when the outlet port is immersed in the liquid.

The linear distal portion of the positionable tube cooperates with the opening in the cap so that the outlet port of the positionable tube can be located at any selected one of a plurality of predetermined, discrete distances below the surface of the liquid and held in place at such selected positions against accidental displacement.

At least one of the positionable tube and the cap includes indicia thereon providing an indication of the pressure of the gas in the positionable tube for each of the plurality of predetermined, discrete distances. The cap also includes a vent opening in communication with the interior of the vessel.

In accordance with one preferred aspect of this invention the apparatus is arranged for effecting respiratory support for a living being by nasal continuous positive airway pressure. In that application the proximal portion of the positionable tube is arranged to be coupled to the downstream side of a pair of nasal prongs or a face mask. The pair of nasal prongs or face mask has an upstream side coupled to the source of gas.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figures 2, 3:
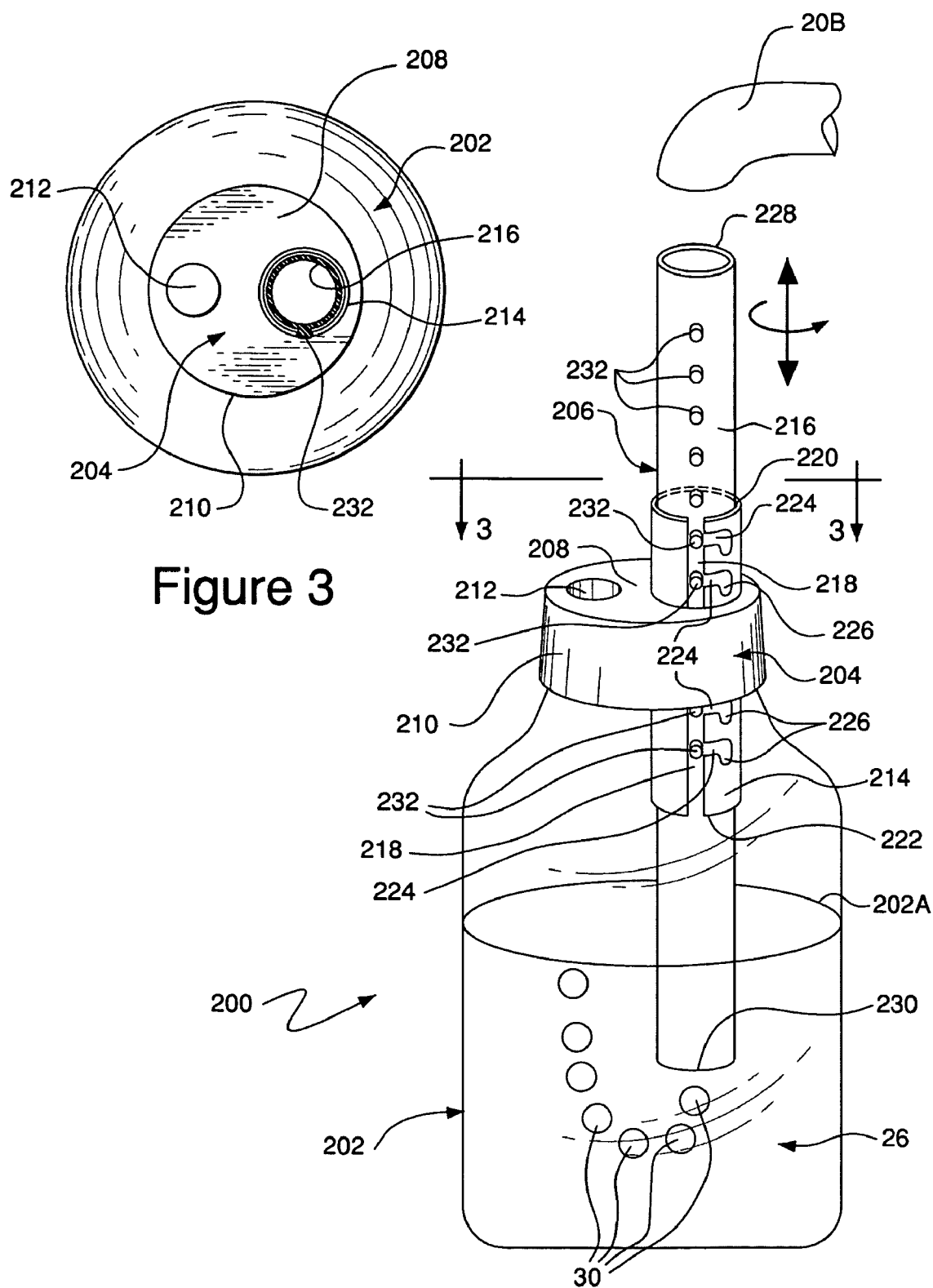
FIG. 2 is an isometric view of one exemplary preferred embodiment of an apparatus for controlling pressure of a gas in a system that depends on the pressure being produced by bubbling the gas through a liquid, e.g., bubble CPAP.
FIG. 3 is an enlarged sectional view taken along line 3—3 of FIG. 2.
Figure 4:
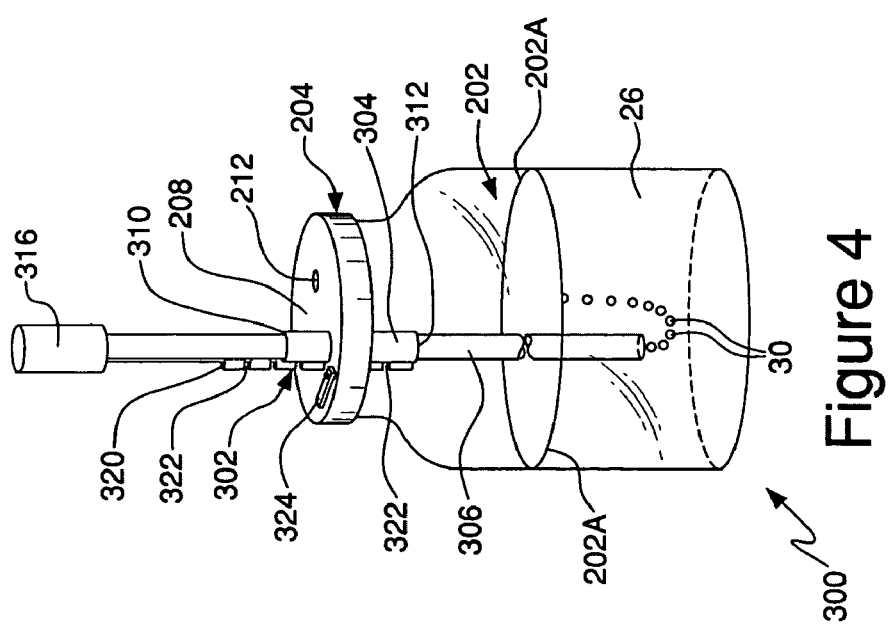
FIG. 4 is a reduced isometric view of another exemplary preferred embodiment of an apparatus for controlling pressure of a gas in a system that depends on the pressure being produced by bubbling the gas through a liquid, e.g., bubble CPAP.
Figure 8:
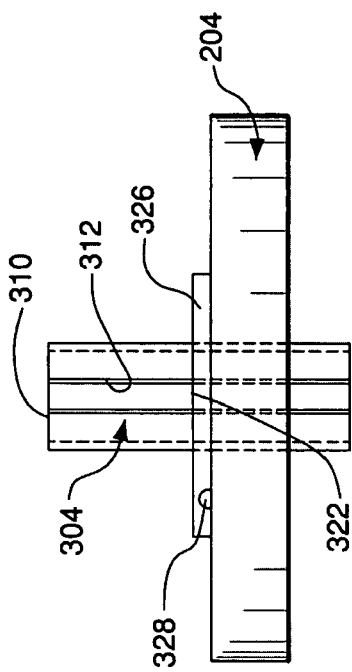
FIG. 8 is a side elevation view of the cap portion of the apparatus shown in FIG. 6.
Figure 7:
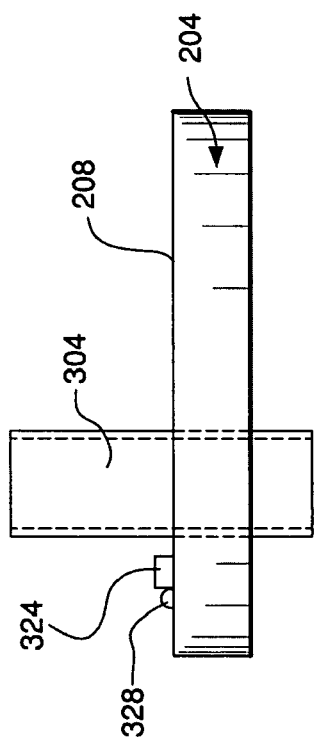
FIG. 7 is a front elevation view of the cap portion of the apparatus shown in FIG. 6.
Figure 6:
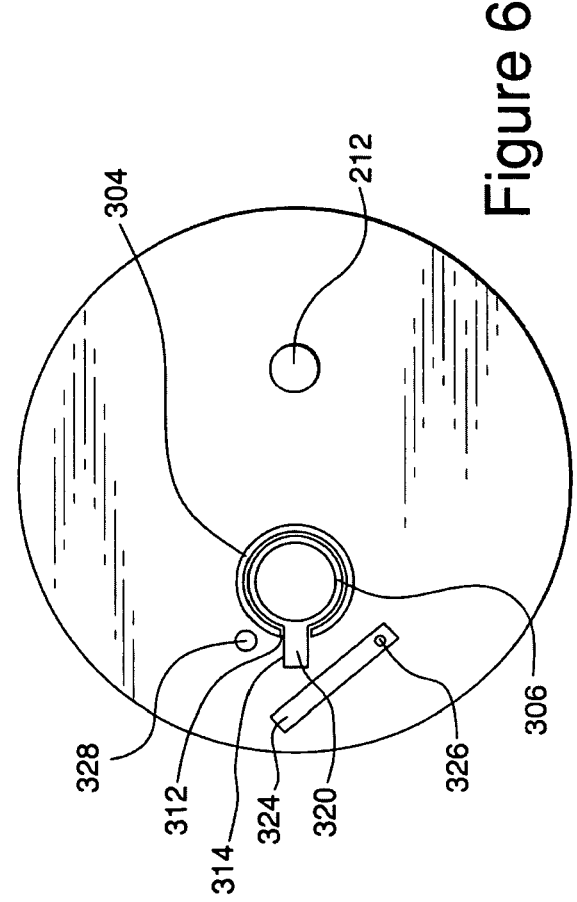
FIG. 6 is a top plan view of the cap portion of the apparatus shown in FIG. 5.

Referring now to the various figures of the drawing wherein like reference characters refer to like parts, there is shown at 200 and 300 in FIGS. 2 and 4, respectively, exemplary embodiments of apparatus for controlling pressure of a gas in a system that depends on the pressure being produced by bubbling the gas through a liquid constructed in accordance with this invention. It should be noted at this juncture that while the apparatus 200 and 300 are particularly suited for effecting bubble CPAP, they can be used of any other application involving controlling pressure of a gas in a system that depends on the pressure being produced by bubbling the gas through a liquid.

Turning now to FIGS. 2 and 3, the details of the construction and operation of the apparatus 200 will now be described. Before doing that, it should be pointed out that if the apparatus 200 is to be used for bubble CPAP, it can be connected in a system like that shown in FIG. 1 in lieu of the bottle 28 and tape strip 32. In the interests of brevity the components of the system 10 that are used along with the apparatus 200 and 300 of this invention to form a bubble CPAP system will be given the same reference numbers as in FIG. 1 and the details of the construction, interconnection and operation of those components will not be reiterated.

As will be seen from the description to follow the apparatus 200 and 300 serve as the means for accurately locating the downstream free end 20C of the ventilator tube 20 at one of a plurality of desired positions (heights) with respect to the surface of the liquid 26 to thereby accurately establish the gas pressure in the ventilator tube 20 and to hold the end of the tube securely in that position to maintain the established gas pressure. To that end the apparatus 200 basically comprises a bottle or other hollow vessel 202, a cap or cover 204, and a positionable tube assembly 206.

The bottle 202 is of conventional construction and includes a hollow interior chamber for receipt of the acetic acid liquid 26 and a upper end or mouth including external threads (not shown). The bottle is filled with the liquid 26 to a predetermined fill line 202A on the bottle. The cap 204 basically comprises a planar top 208 of circular profile from which a lip 210 projects downward. The inner surface of the lip includes an internal helical thread (not shown) for threaded engagement with the external threads on the mouth of the bottle 202 to thereby releasably attach the cap 204 on the bottle.

A vent hole or port 212 is located in the top 208 of the cap adjacent the lip 210 to provide an outlet for the air bubbling up through the liquid. As will be appreciated by those skilled in the art air must be able to egress from the bottle without building up pressure inside the bottle. The vent hole or port 212 provides this function. The size of the hole is not critical. It can be much smaller than the bore of the positionable tube (to be described later) since the length of the vent port is only the thickness of the top 208 of the cap. Keeping the vent hole small also decrease any tendency toward splashing of the acetic acid out from the bottle through the vent hole, which could occur due to the bubbling action when the apparatus 200 is in use.

The positionable tube assembly basically comprises an outer guide tube or collar 214 and an inner positionable tube 216. The guide tube 214 is an elongated tubular member that is oriented so that its longitudinal axis is vertical. The guide tube is fixedly secured to the cap and is located generally opposite to the vent port 212, with a portion of the guide tube 214 extending above the top of the cap. A portion of the guide tube 214 also extends below the cap so that it is located within the hollow interior of the bottle 202. The guide tube includes a slot 218 extending in the longitudinal direction from the top end 220 of the guide tube to the bottom end 222 of the guide tube. Plural transverse recesses or slots 224 are located in the guide tube in communication with the longitudinally oriented slot 218. The plural slots 224 extend transversely to the longitudinal axis of the guide tube, i.e., horizontally, and are equidistantly spaced from one another. In accordance with a preferred embodiment of this invention the spacing between the slots 224 is in 1 cm. increments, but smaller spacing, e.g., 0.5 cm., is contemplated. Each transversely extending slot 224 terminates in a downwardly directed free end portion 226. In accordance with a preferred embodiment of this invention the cap 204 and the guide tube 214 are an integral unit formed of any suitable material, e.g., plastic.

The positionable tube 216 is an elongated generally linear tubular member formed of any suitable material, e.g., plexiglass, whose outside diameter is just slightly less than the inside diameter of the guide tube 214. The bore size (internal diameter) of the positionable tube is not critical as long as it is big enough to avoid significant inadvertent pressure from resistance to flow through the tube. This can be achieved by tubing with the same internal diameter as the ventilator tubing.

The positionable tube 216 is arranged to be located within the guide tube 214 and to be slid longitudinally with respect thereto to establish the gas mixture pressure in the ventilator tube. To that end the positionable tube 216 has an upper end portion 228 which is arranged to be connected to the downstream end of the ventilator tube section 20B by any suitable adaptor (not shown in this embodiment, but of the same construction as adaptor 316 shown and described later with respect to apparatus 300). The positionable tube 216 is substantially longer than the guide tube 214 so that when it is located within the guide tube its upper end portion 228 extends above the top end of the guide tube and its lower or free end 230 extends below the lower free end of the guide tube and into the liquid 26. Thus, the lower free end 230 of the positionable tube 216 acts as the heretofore identified free end 20C of the ventilator tube.

The depth of the bottle 26 is preferably sufficiently deep to accommodate the positionable tube's free end 230 to a depth that produces a pressure of 10 centimeters without obstructing gas flow from the positionable tube. This provides adequate ability to set the pressure as high as would be practical. The diameter of the bottle should be a convenient size for fixing it with some type of clamp to an IV pole or similar supporting device to prevent tipping.

In order to effect the desired positioning of the positionable tube 216 with respect to the guide tube 214 and to hold it in that desired position, the positionable tube includes at least one and preferably a plurality of disk-like buttons or projections 232 projecting outward from the exterior surface of the positionable tube 216. The projections are located so that they extend linearly along the longitudinal axis of the positionable tube for at least a substantial portion of the length of that tube. The projections 232 are sized to be received within the longitudinally extending slot 218 in the guide tube 214 and also into any of the communicating transversely extending slots 224.

Use of the apparatus 200 to establish a desired pressure in the ventilator tube is as follows. The bottle 28 is filled with the desired amount of liquid 26 and the cap placed on the bottle. The positionable tube is disposed in the guide tube from the top end thereof and so that the line of projections 232 is aligned with the slot 218. The positionable tube can then be pushed inward (downward) so that the projections 232 align with selected ones of the transversely extending slots 224 such that the free end 230 of the positionable tube 216 is a desired depth in the liquid 26. Indicia in the form of a scale (not shown) are provided on the guide tube and/or the positionable tube to designate the number of centimeter (or half-centimeters if the apparatus is manufactured to achieve that degree of precision) that the positionable tube will be below the level of the liquid. Once the positionable tube is at the desired vertical position with respect to the guide tube and its projections 232 aligned with the transversely extending slots 224, the positionable tube is rotated in the direction of the arcuate arrow in FIG. 2 to cause those projections to slide into the transversely extending slots 224. When the projections 232 reach the inner free end portions 226 of the transverse slots a slight downward pressure on the positionable tube causes them to drop into those portions of the slots. This action releasably locks the positionable tube in place against accidental displacement.

Figure 1:
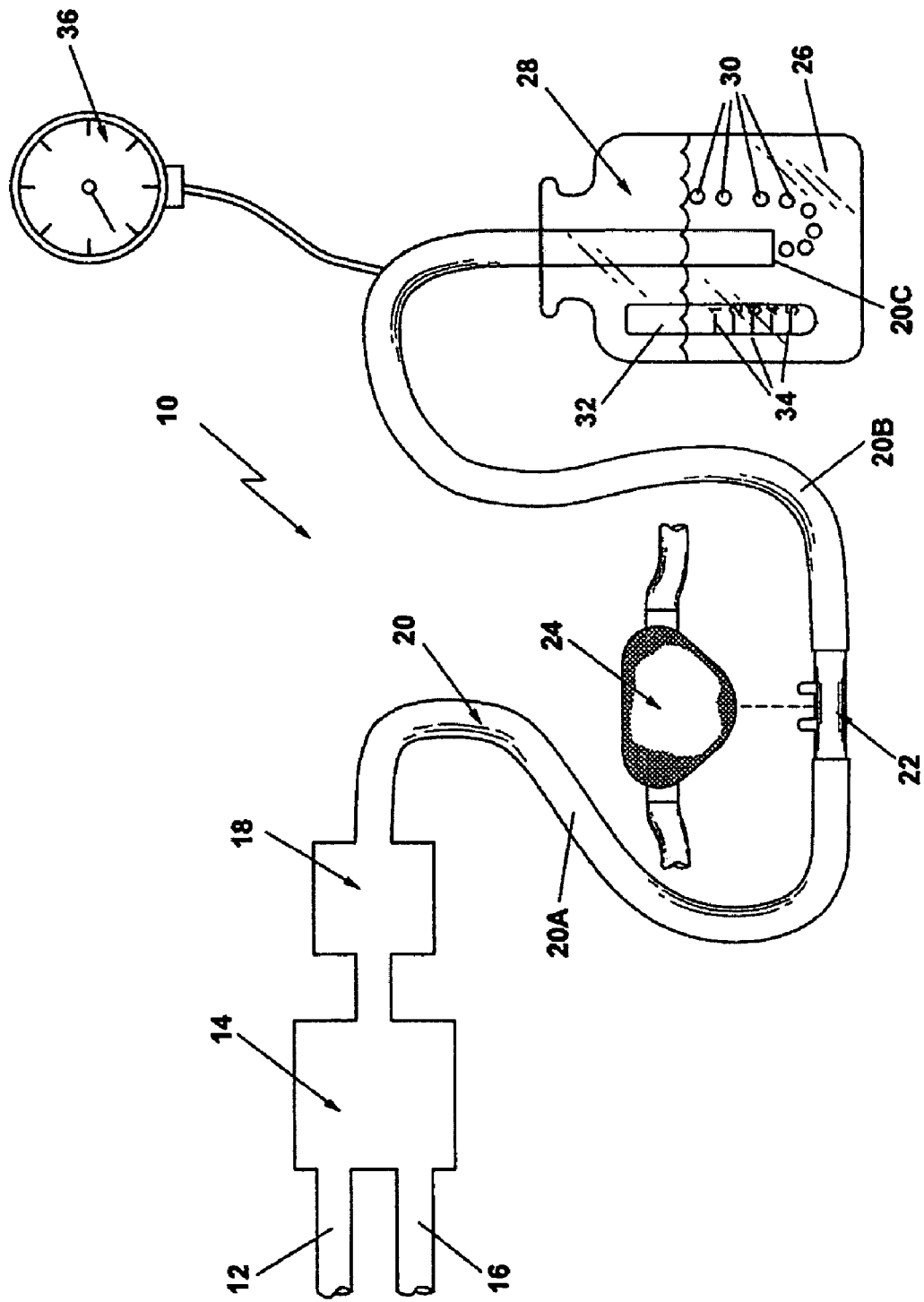
FIG. 1 is a schematic diagram of a conventional prior art system for effecting bubble CPAP.

The apparatus 200 can now be used in the bubble CPAP system like that of FIG. 1.

It should be pointed out at this juncture that the best method of insuring accurate pressures using the apparatus 200 is to provide a bottle 202 of specific dimensions as part of the apparatus 200. This insures that the specially designed bottle cap 204 will fit, which is clearly important. It also allows for accurate factory calibration to be accomplished during manufacturing of the apparatus. The need for calibration, as opposed to placing the slots exactly one centimeter apart, arises because as air displaces fluid from the positionable tube, the fluid level will rise in the bottle changing the true depth of insertion. The correction for the rise in fluid level (the calibration) is easily done for the entire system when the system is designed by calculating how much the fluid rises per unit insertion of the inner tube or by measuring and marking the specific depths of insertion that give one centimeter increments in pressure.

If it is desired to change the depth of immersion of the free end 230 of the positionable tube in the liquid, e.g., to raise the tube one centimeter to reduce the gas pressure to the infant by one centimeter of water, all that is required is to pull up on the positionable tube to free the projections from the slot portions 226, whereupon the positionable tube can be rotated about its longitudinal axis in the opposite direction to cause the projections to slide down the transversely extending slots 224 and into the longitudinally extending slot 218. At that point the positionable tube can be pulled upward until the projections are located one transverse slot 224 above their previous positions, thereby moving the positionable tube upward by one centimeter (assuming that the slots 224 are separated from one another by one centimeter). Once the positionable tube is in this position, it can be rotated about its longitudinal axis as described above to cause its projections to ride down the now aligned transversely extending slots 224 into the downwardly directed free end portions 226.

As should be appreciated from the foregoing because the apparatus 200 includes a readily adjustable and reliable locking mechanism for the positionable tube the setup for bubble CPAP becomes more reliable, more accurate and safer. The rest of the bubble CPAP mode of action is unchanged.

In FIGS. 4–8 there is shown an alternative preferred embodiment of the apparatus 300 of this invention. The apparatus 300, is constructed slightly differently than the apparatus 200. Yet it still includes the same basic features of the apparatus 200. In particular, the apparatus 300 makes the use of a bottle having a cap and a positionable tube assembly including a guide tube and a positionable tube which can be readily positioned at any one of a plural discrete positions with respect to the guide tube and held in that position against accidental displacement. In the interests of brevity the common components of the apparatus 200 and 300 will be given the same reference numbers and the details of their construction, arrangement and operation will not be reiterated.

Thus, as can be seen in FIGS. 4–8 the positionable tube assembly 302 basically comprises an outer guide tube or collar 304 and an inner positionable tube 306. The guide tube 304 is an elongated tubular member that is oriented so that its longitudinal axis is vertical and is fixedly secured to the cap 204 with a portion of the guide tube 304 extending above the top of the cap and a portion of the guide tube 304 extending below the cap so that it is located within the hollow interior of the bottle 202. The guide tube 304 includes a slot 312 (FIGS. 6 and 8) extending in the longitudinal direction from the top end 310 of the guide tube to the bottom end 312 of the guide tube. The top 208 of the cap 204 includes a slot 314 (FIG. 6) in it that is in communication with the longitudinally extending slot 312 in the guide tube so that the slot 314 in the cap forms an extension of the slot 312 in the guide tube.

The positionable tube 306 is an elongated generally linear tubular member formed of any suitable material, whose outside diameter is just slightly less than the inside diameter of the guide tube 304. The positionable tube's bore size (internal diameter) is like that of the positionable tube 216 of apparatus 200, i.e., big enough to avoid significant inadvertent pressure from resistance to flow through the tube.

The positionable tube 306 is arranged to be located within the guide tube 304 and to be slid longitudinally with respect thereto to establish the gas mixture pressure in the ventilator tube in a similar manner as discussed with respect to the apparatus 200. To that end, the positionable tube 306 has an upper end portion which is arranged to be connected to the downstream end of the ventilator tube section 20B by any suitable adaptor 316. The positionable tube 306 is substantially longer than the guide tube so that when it is located within the guide tube its upper end portion extends above the top end of the guide tube and its lower or free end 318 extends below the lower free end of the guide tube and into the liquid 26. The lower free end 318 of the positionable tube 306, thus acts as the heretofore identified free end 20C of the ventilator tube.

The positionable tube 306 includes a rib 320 projecting outward from it and extending longitudinally along its middle portion. The rib 320 projects diametrically outward from the tube by a distance that is just slightly less than the length of the slot 314 (see FIG. 6) in the cap 208. The thickness of the rib 320 is just slightly less the thickness of the slot 312 in the guide tube 304. Accordingly, the positionable tube 306 can be disposed within the guide tube 304, with the rib 320 extending through the slot 312 in the guide tube and in the slot 314 in the cap, so that the positionable tube can be slid to various discrete longitudinal positions along the guide tube. In order to establish those discrete longitudinal positions, the rib 320 includes a plurality of equidistantly spaced transversely extending notches or recesses 322. The recesses are spaced at approximately one-centimeter increments from one another but can be in other closer increments, e.g., 0.5 cm.

Figure 5:
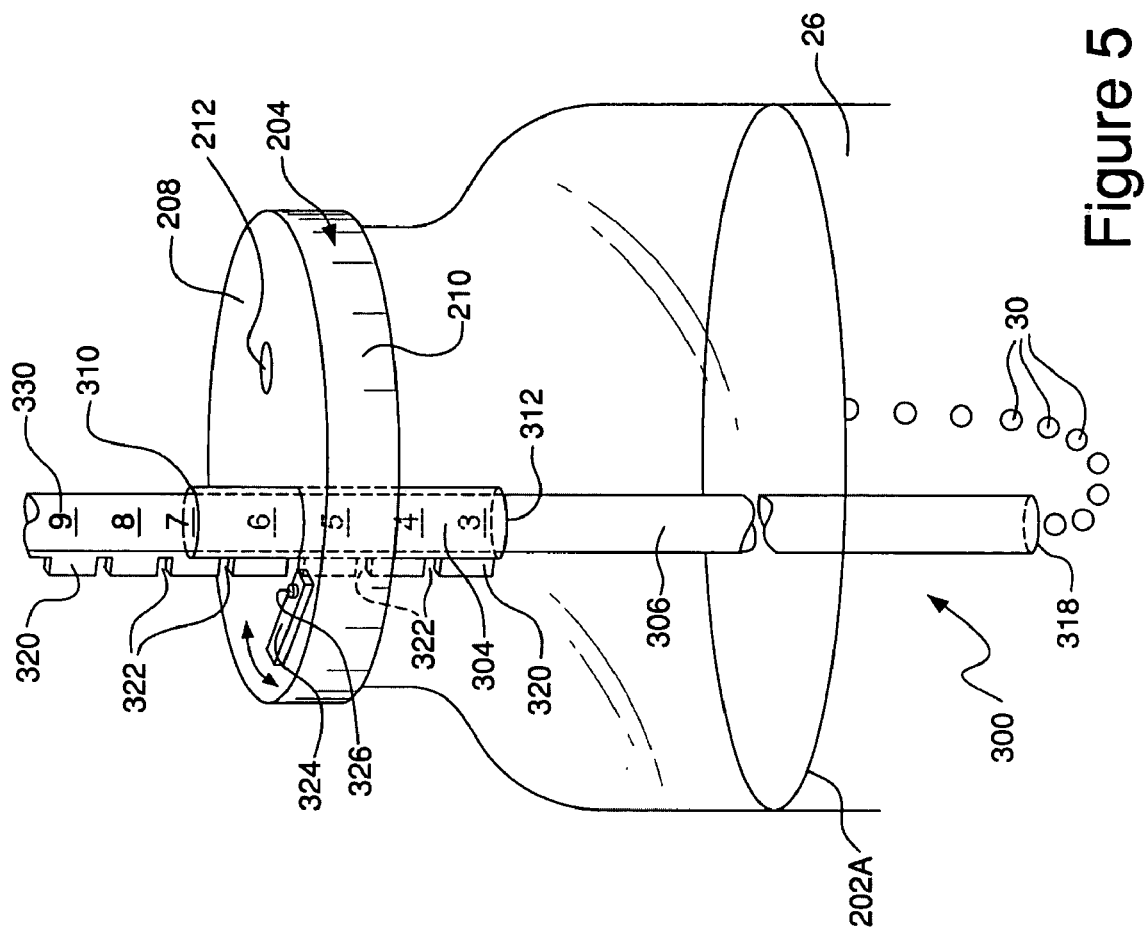
FIG. 5 is an enlarged isometric view of a portion of the apparatus shown in FIG. 4.

Since the positionable tube is slidable within the guide tube, any one of the recesses 322 in the rib 320 can be brought into alignment with the top surface 208 of the cap 204 as shown in FIGS. 4 and 5. A locking lever or arm 324 is mounted on the top 208 of the cap by means of a pivot pin 326. The lever 324 is a generally linear member whose thickness is just slightly less than the width of each of the recesses 322 in the rib 320. The lever 324 is arranged to be pivoted about the pivot pin 326 from an open position, shown in FIG. 6, wherein no portion of the lever is located within any recess 322, to a closed or operative position (FIG. 8), wherein a portion of the lever is located in whatever recess is aligned with the top surface of the cap. This action effectively locks the positionable tube longitudinally with respect to the guide tube, thereby establishing the desired pressure for the bubble CPAP system. The lever 324 is held in position against accidental displacement from the recess 322 in which it is disposed by means of a small button 328 fixedly secured to the top 208 of the cap 204 to hold it in place. In particular, when the lever 324 is pivoted into the aligned recess in the rib 320, the free end of the lever rides over the button 328 so that the button acts as a detent to hold the lever within the recess. When it is desired to change the position of the positionable tube with respect to the guide tube, all that is required is to pivot the lever back over the button 328 and out of the recess 322 in the rib 320. The positionable tube can then be either pulled upward or pushed downward with respect to the guide tube to align any other of its recesses 322 with the top surface of the cap, whereupon the lever can then be pivoted back into that recess in the same manner as just described.

As can be seen in FIG. 5 a scale in the form of numerical indicia 330 is provided on the positionable tube to indicate the depth of immersion of the free end 318 of the positionable tube under the surface of the liquid in the bottle.

It should be pointed out at this juncture that in lieu of a single vent hole or port multiple small holes are can be used in the cap 204 for either apparatus 200 or 300 (or any apparatus constructed in accordance with the teachings of this invention). It should also be pointed out that the specific means for establishing the position of the positionable tube with respect to the opening in the cap (e.g., the bore through the guide tube) as described above are merely exemplary of various arrangements that can be used. For example, the guide tube need not extend below the surface of the cap, so long as there is a sufficient length of guide tube to hold the positionable tube in any of a discrete number of longitudinal positions with respect to the guide tube. In short, this invention contemplates use of any type of means or mechanism for positioning a tube carrying a gas in fixed increments through a cap of a bottle or some other vessel to releasably secure and dispose the lower free end of the tube at any one of plural discrete positions.

While the invention has been described in detail and with reference to specific examples thereof, it will be apparent to one skilled in the art that various changes and modifications can be made therein without departing from the spirit and scope thereof.

What is claimed is:

1. Apparatus for controlling pressure of a gas in a system that depends on the pressure being produced by bubbling the gas through a liquid, said apparatus comprising a hollow vessel, a cap, and a positionable tube, said hollow vessel being arranged to have a predetermined amount of the liquid introduced therein, whereupon the surface of the liquid reaches a predetermined height in said vessel, said cap being located above the surface of the liquid in said vessel and including an opening through which said positionable tube extends, said positionable tube including a proximal portion arranged to be coupled to a source of the gas, whereupon the gas may flow into and through said positionable tube, said positionable tube including a distal portion which is linear and terminates at an outlet port through which the gas may exit to bubble up through the liquid when said outlet port is immersed in the liquid, said positionable tube and said cap being coupled together in such a manner that said linear distal portion of said positionable tube cooperates with said opening in said cap whereupon said outlet port of said positionable tube can be expeditiously located at any selected one of a plurality of predetermined, discrete distances below the surface of the liquid, but not at any intermediate positions between said discrete distances, and held in place at such selected discrete position against accidental displacement, at least one of said positionable tube and said cap including indicia thereon indicating the pressure of the gas in said system for each of said plurality of predetermined, discrete distances, said cap also including a vent opening.

2. The apparatus of claim 1 wherein said apparatus is arranged for effecting respiratory support for a living being by nasal continuous positive airway pressure, and wherein said proximal portion of said positionable tube is arranged to be coupled to the downstream side of a pair of nasal prongs or a mask, the pair of nasal prongs or mask having an upstream side coupled to the source of gas.

3. The apparatus of claim 1 wherein one of said positionable tube and said cap includes a plurality of recesses corresponding to said plurality of predetermined, discrete distances and the other of said positionable tube and said cap includes at least one member arranged to be selectively resident in any one of said plurality of recesses to hold said positionable tube at the selected position.

4. The apparatus of claim 2 wherein one of said positionable tube and said cap includes a plurality of recesses corresponding to said plurality of predetermined, discrete distances and the other of said positionable tube and said cap includes at least one member arranged to be selectively resident in any one of said plurality of recesses to hold said positionable tube at the selected position.

5. The apparatus of claim 3 wherein said cap includes a tubular guide portion through which said distal portion of said positionable tube extends, said tubular guide portion having a longitudinal axis including a slot extending along said axis and a plurality of transverse slots in communication with said longitudinal extending slot, said plurality of slots forming said plurality of recesses.

6. The apparatus of claim 4 wherein said cap includes a tubular guide portion through which said distal portion of said positionable tube extends, said tubular guide portion having a longitudinal axis including a slot extending along said axis and a plurality of transverse slots in communication with said longitudinal extending slot, said plurality of slots forming said plurality of recesses.

7. The apparatus of claim 5 wherein said positionable tube has a longitudinal axis and a plurality of projections extending linearly along said longitudinal axis of said positionable tube for at least a portion of the length of said tube, said projections being sized to be received within said longitudinally extending slot and said transversely extending slots, said transversely extending slots being spaced from each other by said predetermined, discrete distances.

8. The apparatus of claim 6 wherein said positionable tube has a longitudinal axis and a plurality of projections extending linearly along said longitudinal axis of said positionable tube for at least a portion of the length of said tube, said projections being sized to be received within said longitudinally extending slot and said transversely extending slots, said transversely extending slots being spaced from each other by said predetermined, discrete distances.

9. The apparatus of claim 7 wherein each of said transversely extending slots terminates in a portion extending parallel to said longitudinal axis of said guide tube.

10. The apparatus of claim 8 wherein each of said transversely extending slots terminates in a portion extending parallel to said longitudinal axis of said guide tube.

11. The apparatus of claim 3 wherein said cap includes a tubular guide portion through which said distal portion of said positionable tube extends, said tubular guide portion including a longitudinally extending slot, said distal portion of said positionable tube including a longitudinally extending rib, said rib including said plurality of recesses.

12. The apparatus of claim 4 wherein said cap includes a tubular guide portion through which said distal portion of said positionable tube extends, said tubular guide portion including a longitudinally extending slot, said distal portion of said positionable tube including a longitudinally extending rib, said rib including said plurality of recesses.

13. The apparatus of claim 11 wherein said cap includes a movable member adapted to move into a selected one of said plurality of recesses.

14. The apparatus of claim 12 wherein said cap includes a movable member adapted to move into a selected one of said plurality of recesses.

* * * * *